(12) United States Patent
Divi et al.

(10) Patent No.: US 11,407,779 B1
(45) Date of Patent: Aug. 9, 2022

(54) PROCESS FOR THE PREPARATION OF MOLNUPIRAVIR

(71) Applicant: DIVI'S LABORATORIES LTD., Telangana (IN)

(72) Inventors: Murali Krishna Prasad Divi, Telangana (IN); Mysore AswathaNarayana Rao, Telangana (IN)

(73) Assignee: DIVI'S LABORATORIES LTD., Hyderabad (IN)

( * ) Notice: Subject to any disclaimer, the term of this patent is extended or adjusted under 35 U.S.C. 154(b) by 0 days.

(21) Appl. No.: 17/362,098

(22) Filed: Jun. 29, 2021

(30) Foreign Application Priority Data

Apr. 23, 2021 (IN) .............................. 202141018775

(51) Int. Cl.
*C07H 1/00* (2006.01)
*C07H 19/067* (2006.01)

(52) U.S. Cl.
CPC ............. *C07H 1/00* (2013.01); *C07H 19/067* (2013.01)

(58) Field of Classification Search
CPC .............................. C07H 1/00; C07H 19/067
See application file for complete search history.

(56) References Cited

FOREIGN PATENT DOCUMENTS

| CN | 112552288 A | 3/2021 |
| CN | 112608357 A | 4/2021 |

OTHER PUBLICATIONS

Gopalsamuthiram et al. (2021). A Concise Route to MK-4482 (EIDD-2801) from Cytidine: Part 2. Synlett, 32(03), 326-328.
Extended European Search Report from corresponding EP 21186385.7 dated Dec. 14, 2021.
English Abstract for CN 112552288 A (2021).
English Abstract for CN 112608357 A (2021).
Indian Examination Report dated Jun. 28, 2021.

*Primary Examiner* — Jonathan S Lau
(74) *Attorney, Agent, or Firm* — Caesar Rivise, PC

(57) ABSTRACT

A process for the preparation of Molnupiravir, an antiviral drug under investigation for the treatment of Covid-19, is provided including reacting 2'-3'-isopropylidene cytidine with isobutyric anhydride in the presence of a base to obtain 5'-isobutyric ester having an amide impurity. Treating the reaction mixture with para-toluenesulphonic acid monohydrate results in acetonide deprotection giving pure isobutyric cytidine tosylate salt which is free from the amide impurity. Conversion of tosylate salt into free base and reacting with hydroxylamine gives Molnupiravir.

6 Claims, No Drawings

PROCESS FOR THE PREPARATION OF MOLNUPIRAVIR

CROSS-REFERENCE TO RELATED APPLICATIONS

This application claims priority to Indian Patent App. No. 202141018775, filed Apr. 23, 2021, the contents of which are hereby incorporated by reference in their entireties.

FIELD OF INVENTION

The present invention relates to an improved process for the preparation of Molnupiravir (MK-4482, earlier known as EIDD-2801), an orally active antiviral agent which is being investigated for treating COVID-19 infection.

BACKGROUND OF THE INVENTION

Molnupiravir is chemically [(2R,3S,4R,5R)-3,4-dihydroxy-5-[4-(hydroxyamino)-2-oxopyrimidin-1-yl]oxolan-2-yl]methyl 2-methylpropanoate, having the structure (I):

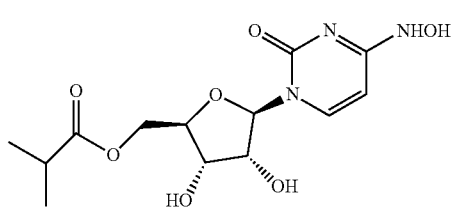

Molnupiravir was discovered at Emory University and is undergoing clinical development in partnership with Ridgeback Biotherapeutics and Merck & Co.

The first synthetic route reported for Molnupiravir used uridine as the starting material which is expensive and of limited availability [WO2019113462; WO2019173602]. Furthermore, the route suffered from low yields. Compared to uridine, cytidine is less expensive and direct transamination of cytidine with hydroxylamine is possible. Hence new routes based on cytidine have been reported (Schemes 1 & 2).

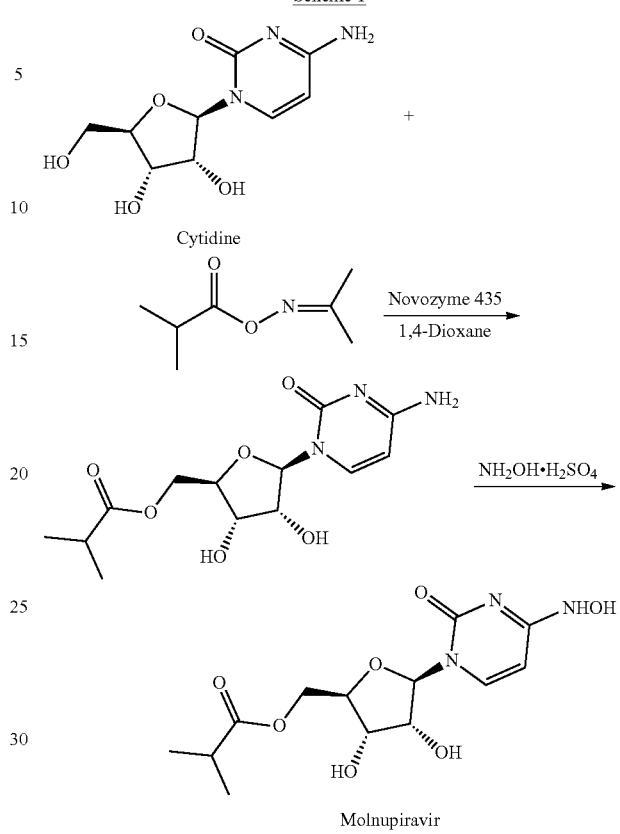

Scheme 1

Scheme 1 discloses selective esterification of the primary alcohol of cytidine with isobutyryl acetone oxime ester using Novozyme 435 which is immobilized Candida antarctica Lipase B. In the next step, the cytidine ester was reacted with hydroxylamine sulphate to obtain molnupiravir (Chem. Commun. 2020, 56, 13363-13364). The use of immobilized enzyme makes the scheme expensive. Furthermore, some amounts of di and tri ester impurities are formed, in spite of using the enzyme, during the first stage and partial deamination was observed in the second stage. Both stages require purification through column chromatography.

Scheme 2 adopted chemical approach to selectively esterify primary alcohol of cytidine, instead of the enzyme system.

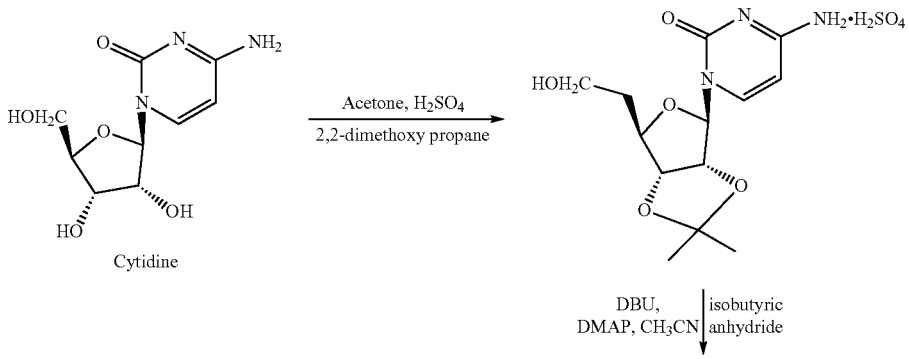

Scheme 2

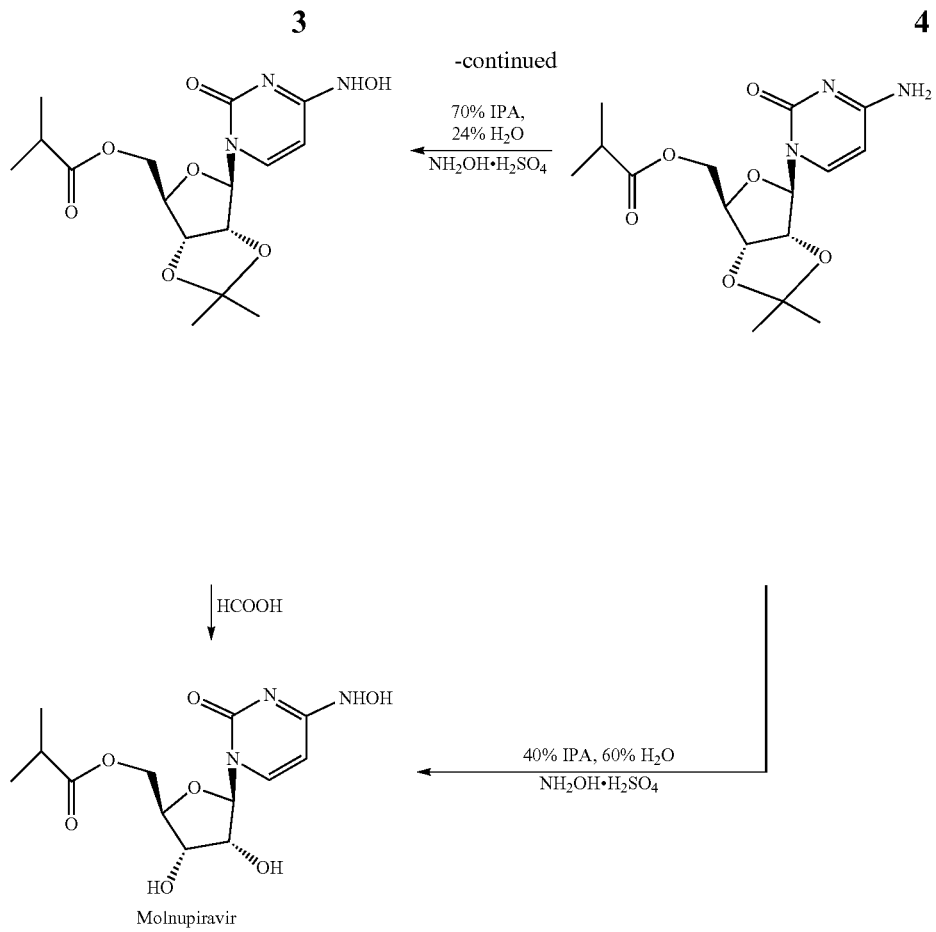

Cytidine was reacted with acetone, sulfuric acid and 2,2-dimethoxy propane to obtain 2',3'-O-isopropylidene cytidine sulfate. It was reacted with isobutyric anhydride in the presence of 1.8-diazabicyclo[5.4.0]undec-7-ene (DBU) and catalytic amount of 4-dimethylaminopyridine (DMAP) in acetonitrile. The resulting cytidine acetonide ester was reacted with hydroxylamine sulfate in 70% IPA (24% water by KF titration), followed by deprotection of acetonide using formic acid to give Molnupiravir. The final product was isolated using column purification in 64% yield. Alternatively, the cytidine acetonide ester was directly converted into molnupiravir by carrying out both hydroxylamination and acetonide deprotection in one step by treating with hydroxylamine sulfate in 40% IPA (60% water) for a longer time. However, this resulted in significant hydrolysis of the ester leading to the formation of about 20% N-hydroxycytidine as a byproduct (Synlett.2021, 32(3), 326-328).

Another major drawback of the Scheme 2 is that we observed release of carbon monoxide during the reaction with formic acid used in acetonide deprotection. Use of formic acid for deprotection of acetonide is reported in several literature (WO2019113462; WO2019173602; WO 2016/106050A1). However, it is also known in the literature that formic acid is a source of carbon monoxide and mere storing it for a longer time results in the liberation of carbon monoxide (containers are to be vented frequently).

Thus, both the schemes based on cytidine have certain drawbacks and there is a need for a safer alternative process.

SUMMARY OF THE INVENTION

While studying the esterification of 2',3 '-O-isopropylidene cytidine sulfate (II) with butyric anhydride in the presence of base, it was observed that, in addition to 5'-isobuturyl cyti dine acetonide (III), about 8% amide is forming as a byproduct (Impurity-1) due to the cross-reaction of the amino group of the cytidine, (Scheme 3).

As a method of purification, without using column chromatography, salt formation with various acids were investigated. When para-toulenesulphonic acid (PTSA) which is a monohydrate was used for the salt formation, besides obtaining pure salt which was free from the amide impurity, deprotection of the acetonide group was also observed and directly 5'-isobutyrylcytidine tosylate ((IV) was obtained (Scheme 3).

The importance of the water of crystallization is further demonstrated by the fact that azeotroped PTSA was unable to hydrolyze the acetonide group, albeit it could form a tosylate salt.

It was also a pleasant surprise to note that the water of crystallization present in the acid was hydrolyzing only the acetonide group without affecting the isobuturyl ester group present in the molecule.

The tosylate salt (IV) was converted to 5-isobutyryl cytidine free base (V), and on reaction with hydroxylamine gives Molnupiravir (I).

The main advantage of the present process is avoiding formic acid for acetonide deprotecti on which is a source of carbon monoxide and achieving the purification without using column chromatography.

Scheme 3

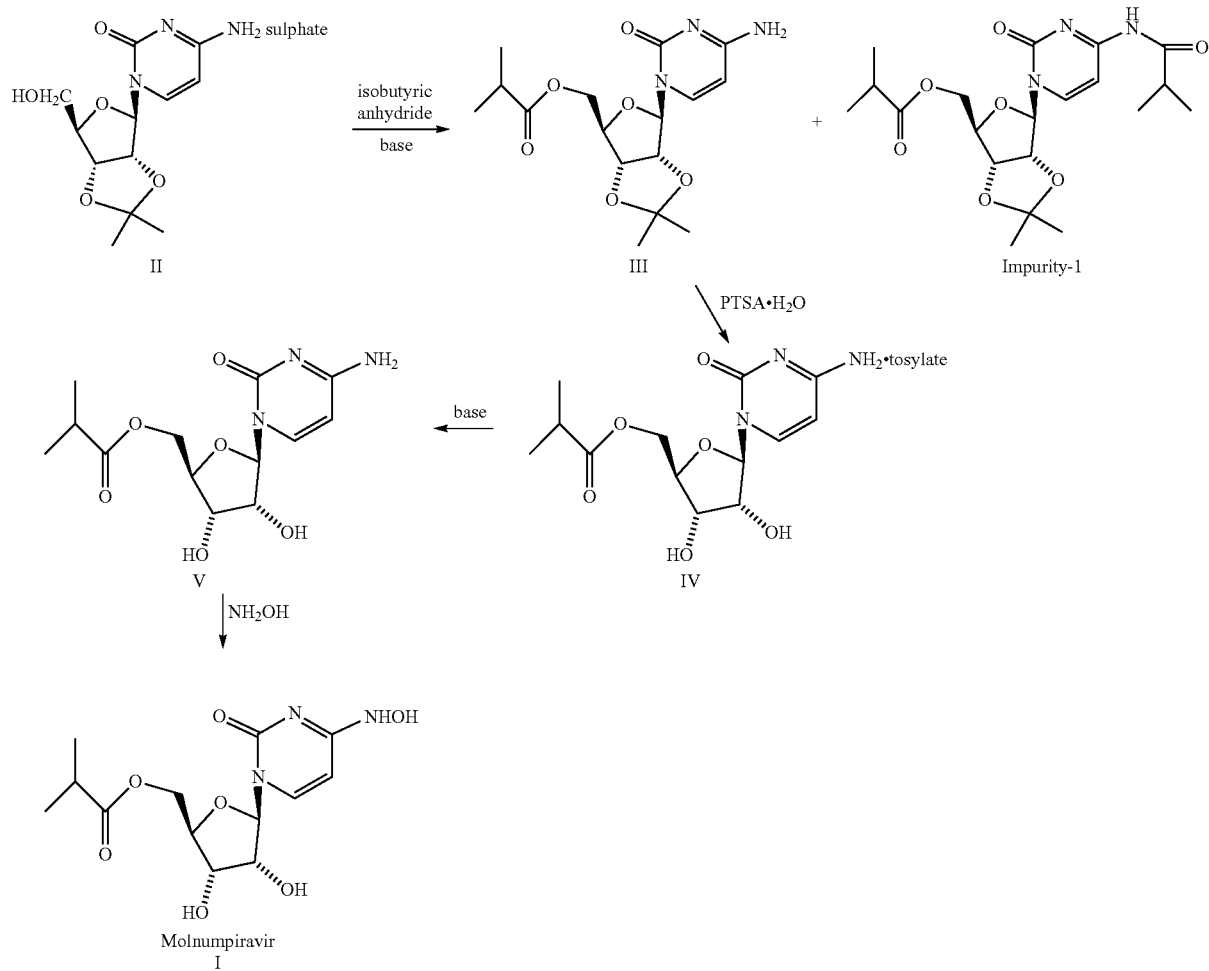

DETAILED DESCRIPTION OF THE INVENTION

The present invention provides a novel process for the preparation of Molnupiravir which comprises the steps of:
(a) reacting 2',3'-O-isopropylidene cytidine sulphate having the structure II,

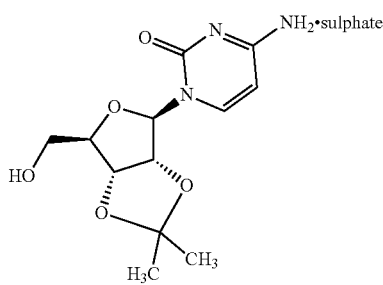

with isobutyric anhydride in a solvent in the presence of a non-nucleophilic base at room temperature to obtain 5-isobutyric ester of the structure (III), having N-isobutyric amide as an impurity (Impurity 1),

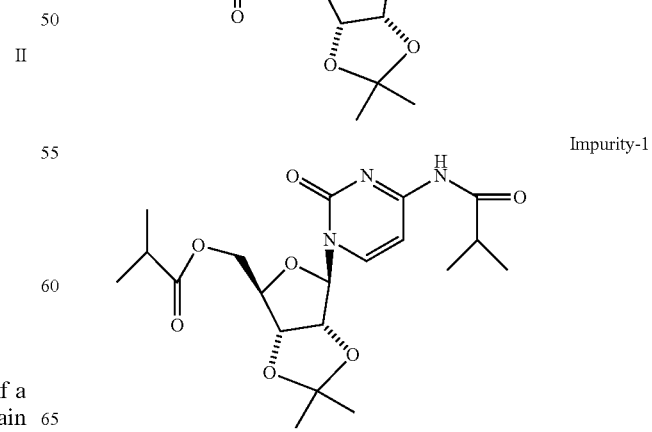

(b) reacting the reaction product obtained from step-a with para-toluenesulphonic acid monohydrate to obtain 5'-isobutyryl cytidine acid tosylate salt (IV), which is free from N-isobutyric amide impurity, and

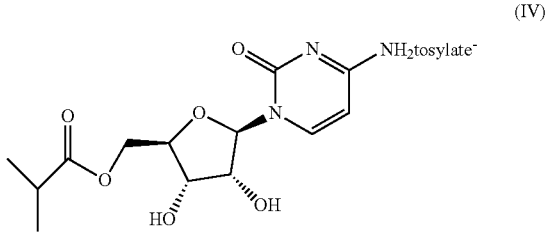

(IV)

(c) converting 5'-isobutyryl cytidine acid salt (IV) to its free base (V) and reacting the free base with hydroxylamine to obtain Molnupiravir (I).

The required starting material, 2',3'-O-isopropylidene cytidine sulphate of formula (II), can be prepared by the method as described in Synlett (2021), 32(3), 326-328.

Esterification of (II) with isobutyric anhydride in the presence of a non-nucleophilic base gives the isobutyric ester (III). The reaction can be carried out in acetonitrile at room temperature. The non-nucleophilic bases that can be used are, triethylamine, diisopropylethyl amine (DIPEA), 1,8-diazabicyclo[5.4.0]undec-7-ene (DBU), N-methyl morpholine (NMM), and 1,4-diazabicyclo-[2.2.2]octane (DABCO). Addition of catalytic amount of 4-dimethylaminopyridine enhances the reaction. The reaction takes about 18-24 hours for the completion after which it is concentrated and the residue is stirred with a mixture of water and dichloromethane for about 5 minutes. After separating the layers, the organic layer is dried and concentrated to get a foamy solid which contains about 90% yield of (III). The residue also contains Impurity-1, in about 8%, which is an amide derivative and an unknown Impurity-2 in about 0.5% in HPLC analysis.

Treating the above residue with para-toluenesulphonic acid monohydrate, resulted in obtaining 5'-isobutyryl cytidine tosylate along with the acetonide hydrolysis. The reaction can be conducted in ethyl acetate or acetonitrile. At room temperature, only tosylate salt is formed. However, when the reaction is conducted at 75-80° C. for about 24 hours, the acetonide moiety gets hydrolysed to form (IV) having 98% purity by HPLC. It was completely free from Impurity-1 and the Impurity-2 was reduced to about <0.05%. The hydrolysis of the acetonide was caused by the water of crystallization present in para-toluenesulphonoc acid monohydrate which is about 12%. The PTSA after azeotrope in xylene was ineffective to cause the hydrolysis of acetonide. Drying PTSA monohydrate in desiccator did not decrease the water content. When acetonitrile was used as solvent, about 5% hydrolysis of ester was observed. Reacting the tosylate salt (IV) with a base gives 5'-isobutyryl cytidine (V). Although various organic bases can be used, best results was obtained when dicyclohexylamine (DCHA) was used. Treating IV with DCHA, about 1 to 1.5 equivalent, in acetone at room temperature for about an hour, results in the precipitation of PTSA.DCHA salt which is removed by filtration. The filtrate is concentrated and the residue is treated with water and dichloromethane, to remove the residual PTSA-DCHA salt and remaining free DCHA.

Reaction of cytosine derivatives with hydroxylamine to obtain N-hydroxy cytosines is known since 1965 (Biochemical & Biophysical research Communications, 18(4), 1965,617-622).

The free base of cytidine butyrate(V) can be converted into molnupiravir by reacting with hydroxylamine. The reaction can be conducted using commercially available salts of hydroxylamine such as either HCl or sulphate. Completion of the reaction requires 3 to 5 moles of hydroxylamine and heating at 70 to 80 ° C. for 15 to 20 hours.

The embodiments of the present invention are further described in the following examples, which are not intended in any way to limit the scope of the invention.

EXAMPLES

Example-1: Preparation of 5-isobutyrylcytidine Tosylate (IV)

Cytidine acetonide sulphate (II) (22 g, 57.69 mmol), 4-dimethylaminopyridine (1.41g, 0.2 equiv.), 1.4-diazabicyclo[5.4.0]undec-7-ene (27.23g, 3.1 equiv.), were dissolved in acetonitrile (220 mL) and isobutyric anhydride (14.6g, 1.6 equiv.) was added during 15 min. The solution was stirred for 20h. The reaction mixture was concentrated and the residue was treated with water (100 mL) and dichloromethane (100 mL). After stirring for 5 minutes, the two layers were separated and the organic layer was dried over anhydrous sodium sulphate and concentrated to get 20.9 g foamy solid containing 89.7% III, 8.54% Impurity-1 and 0.54% an unknown impurity-2.

The above solid was dissolved in ethyl acetate (100 mL), to this was added a solution of para-toluenesulphonic acid monohydrate (10.98 g, 1.0 equiv.) in ethyl acetate (100 mL). The reaction mixture was heated to 75-80° C. and stirred for 24h. After cooling to room temperature, the precipitated solids were filtered and washed with ethyl acetate (100 mL), dried under vacuum for 4 hours to obtain 21.5 g (76.7%) IV. Purity by HPLC: 98.53%, tosylate salt of III: 0.24%, Impurity-1: nil, Impurity-2: 0.03%

FT-IR (KBr, cm$^{-1}$): 3481, 3415, 3282, 3137, 2923, 1724, 1690, 1542, 1497, 1453, 1420, 1397, 1331, 1280, 1243, 1198, 1172, 1138, 1126, 1099, 1035, 1010, 919, 875, 830, 814, 765, 683, 622, 585, 567, 527. $^1$H-NMR (300 MHz, DMSO-d$_6$): δ 9.50 (s, 1H), 8.44 (s, 1H), 7.95-7.93 (d, 1H), 7.50-7.46 (d, 2H, Ar-H), 7.13-7.10 (d, 2H, Ar-H), 6.12-6.09 (d, 1H), 5.71-5.69 (d, 1H), 4.33-4.20 (m, 2H), 4.12-4.04 (m, 2H), 3.93-3.89 (m, 1H), 2.64-2.54 (m, 1H), 2.29 (s, 3H), 1.11-1.05 (d, 6H). $^{13}$C-NMR (75 MHz, DMSO-d$_6$): δ 176.40, 159.64, 147.65, 145.05, 144.87, 138.82, 128.76, 125.93, 94.65, 90.99, 81.64, 73.73, 69.71, 63.90, 33.60, 21.25, 19.24, 19.19. ESI-MS: 314.18 [M+H]$^+$ (Free base M.W.: 313.31).

Example-2: Preparation of 5-isobutyrylcytidine Tosylate (IV) in Two Stages

Cytidine acetonide sulphate (II) (30.3 g), 4-dimethylaminopyridine (1.94 g, 0.2 equiv.), 1.4-diazabicyclo[5.4.0]undec-7-ene (37.5 g, 3.1 equiv.), were dissolved in acetonitrile (300 mL) and isobutyric anhydride (20.1 g, 1.6 equiv.) was added dropwise and the reaction was completed as described in Example-1 to obtain 29.1 g foamy solid containing 88.17% (III), 7.31% Impurity-1 and 0.43% an unknown impurity-2 in HPLC analysis.

The above solid was dissolved in ethyl acetate (150 mL), to this was added a solution of para-toluenesulphonic acid monohydrate (17.23 g, 1.1 equiv.) in ethyl acetate (100 mL). The reaction mixture was stirred at 25 to 30 ° C. for one hour and the precipitated solids were filtered and washed with ethyl acetate (100 mL), dried under vacuum for 4 hours to obtain 32.8 g (78.54%) of tosylate salt of III. Purity by HPLC: 97.4%, IV: 1.98%, Impurity-1: nil. M.R: 160-169° C.

FT-IR (KBr, cm$^{-1}$): 3256, 3059, 2987, 2941, 2786, 1731, 1702, 1660, 1543, 1496, 1458, 1409, 1388, 1373, 1352, 1326, 1265, 1252, 1233, 1205, 1191, 1166, 1154, 1124, 1111, 1092, 1072, 1034, 1009, 970, 899, 868, 817, 755, 681, 623, 593, 577, 564, $^{1}$H-NMR (300 MHz, DMSO-d$_{6}$): δ 9.51 (s, 1H), 8.42 (s, 1H), 8.00-7.98 (d, 1H), 7.49-7.47 (d, 2H, Ar-H), 7.13-7.10 (d, 2H, Ar-H), 6.08-6.06 (d, 1H), 5.80-5.79 (d, 1H), 5.07-5.04 (dd, 1H), 4.80-4.77 (dd, 1H), 4.36-4.32 (m, 1H), 4.28-4.17 (m, 2H), 2.54-2.47 (m, 1H and DMSO), 2.29 (s, 3H), 1.49 (s, 3H), 1.29 (s, 3H), 1.08-1.05 (d, 6H). $^{13}$C-NMR (75 MHz, DMSO-d$_{6}$): δ 176.27, 159.93, 147.68, 146.80, 145.46, 138.55, 128.68, 125.93, 113.63, 94.44, 85.48, 84.38, 81.12, 64.21, 33.51, 27.32, 25.54, 21.25, 19.19, 19.10. ESI-MS: 354.12 [M+H]$^{+}$ (Free bas M.W.: 353.37).

The above solid, tosylate salt of III (32.7g), was suspended in ethyl acetate (300 mL) and heated to 75-80° C. and stirred for 20-24 hours. After cooling to room temperature, the solids were filtered and washed with ethyl acetate (100 mL) and acetone (100 mL), dried under vacuum for 3-4 hours to obtain 21.5 g of IV. Purity by HPLC: 98.8%, O-isopropylidene cytidine-5 isobutyrate (III): 0.16%.

Example-3: Preparation of 5-isobutyrylcytidine Tosylate (IV)

The experiment was carried out as described in Example-1, except that the solvent ethyl acetate was replaced with acetonitrile (Yield: 80.6%; Purity by HPLC: 98.6%).

Example-4: Preparation of 2',3'-O-isopropylidene Cytidine-5'-isobutyrate (III)

Cytidine acetonide sulphate (II) (3 g), 4-dimethylaminopyridine (0.19 g, 0.2 equiv.), diisopropylethylamine (DIPEA) (3.15 g, 3.1 equiv.), were dissolved in acetonitrile (30 mL) and isobutyric anhydride (3.15 g, 1.6 equiv.) was added during 15 min. The solution was stirred for 16 hours. The reaction mixture was concentrated and the residue was treated with water (100 mL) and dichloromethane (100 mL). After stirring for 5 minutes, the two layers were separated and the organic layer was dried over anhydrous sodium sulphate and concentrated to get 2.6 g (95%) (III). Purity by HPLC: 83.15%; 9.04% Impurity-1 and 0.31% an unknown impurity-2

Example-5: Preparation of Cytidine-5'-isobutyrate Free Base (V)

Cytidine-5'-isobutyrate tosylate salt (IV) (15 g, 0.031 mol) was suspended in acetone (300 mL) and stirred. To the suspension was added dicyclohexylamine (6.72 g, 0.037 mol) and stirring continued for 2 hours. The precipitated salt of dicyclohexylammonium tosylate was removed by filtration. The solids were washed with acetone (50 mL). The acetone filtrates were pooled and concentrated under reduced pressure. The residue was dissolved in water (100 mL) and washed with dichlormethane (2×100 mL). The aqueous solution was concentrated under reduced pressure and the solid residue obtained was azeotroped with acetone to get 8.3 g (85%Y) of foamy solid (V). Purity by HPLC: 99.5%.

Example-6: Preparation of Cytidine-5'-isobutyrate Free Base (V)

The experiment was carried out as described in Example-4, except that acetone was replaced with 1,4-Dioxane to obtain 7.8 g (80.6%Y) of V. Purity by HPLC: 98.6%. cl Example-7: Preparation of Molnupiravir (I)

Isobutyrylcytidine (V) (5.0g, 0.15 mmol) was suspended in 70% isopropyl alcohol and added hydroxylamine sulphate (8.4 g, 0.51 mmol). The reaction mixture was heated to 75-80° C. for 16 hours. The isopropyl alcohol layer was separated and concentrated under reduced pressure. The residue was dissolved in isopropyl alcohol (60 mL) and removed the undissolved matter by filtration and the filtrate was concentrated and the residue was again dissolved in isopropyl alcohol at 50° C. The clear solution was cooled and the solids filtered to obtain 3.7 g (71%) (I) as colourless solid, HPLC: 99.29.

What is claimed is:

1. A process for the preparation of Molnupiravir having the formula (I),

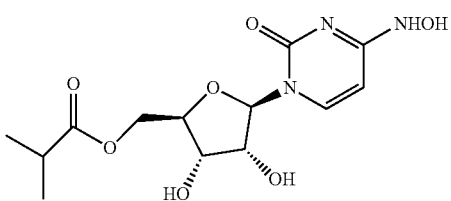

comprising:
(a) reacting 2',3'-O-isopropylidene cytidine sulphate having the structure II,

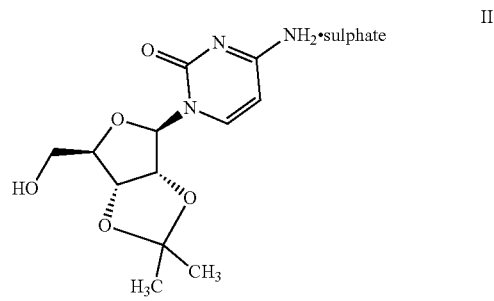

with isobutyric anhydride in a solvent in the presence of a non-nucleophilic base at room temperature to obtain 5-isobutyric ester of the structure (III), having N-isobutyric amide as an impurity (Impurity-1),

III

[Structure of compound III: 5'-isobutyryl-2',3'-O-isopropylidene cytidine]

Impurity-1

[Structure of Impurity-1: N-isobutyryl derivative of compound III]

(b) reacting the reaction product obtained from step (a) with para-toluenesulphonic acid monohydrate to obtain 5'-isobutyryl cytidine acid tosylate salt (IV), which is free from N-isobutyric amide impurity, and

(IV)

[Structure of compound IV: 5'-isobutyryl cytidine tosylate salt]

(c) converting 5'-isobutyryl cytidine acid salt (IV) to its free base (V)

(V)

[Structure of compound V: 5'-isobutyryl cytidine free base]

and reacting (V) with hydroxylamine to obtain Molnupiravir having the structure (I).

2. The method as claimed in claim 1, wherein at step (a), the non-nucleophilic base is a member selected from the group consisting of diisopropylethyl amine (DIPEA), N-methyl morpholine, 1,4-diazabicyclo-[2.2.2]octane (DABCO), 1,8-diazabicyclo[5.4.0]undec-7-ene (DBU) and triethylamine.

3. The method as claimed in claim 1, wherein at step (b), the reaction is conducted at a temperature of 50° C. to 90° C.

4. The method as claimed in claim 1, wherein at step (b), the para-toluene sulphonic acid monohydrate has 8 to 15% water of hydration.

5. The method as claimed in claim 1, wherein at step (c), the 5'-isobutyryl cytidine acid salt (IV) is converted into the free base (V) using dicyclohexylamine.

6. The method as claimed in claim 1, wherein at step (c), the 5'-isobutyryl cytidine acid salt (IV) is converted into the free base (V) using acetone or 1,4-dioxane as the solvent.

\* \* \* \* \*